(12) United States Patent
Hsu et al.

(10) Patent No.: US 12,171,460 B2
(45) Date of Patent: Dec. 24, 2024

(54) COMPUTER-ASSISTED NEEDLE INSERTION SYSTEM AND COMPUTER-ASSISTED NEEDLE INSERTION METHOD

(71) Applicant: Industrial Technology Research Institute, Hsinchu (TW)

(72) Inventors: Po-An Hsu, New Taipei (TW); Chih-Chi Chang, Hsinchu (TW); Chih-Wei Chien, Nantou County (TW); Chia-Pin Li, Taichung (TW); Kun-Ta Wu, Nantou County (TW); Wei-Zheng Lu, Chiayi (TW)

(73) Assignee: Industrial Technology Research Institute, Hsinchu (TW)

( * ) Notice: Subject to any disclaimer, the term of this patent is extended or adjusted under 35 U.S.C. 154(b) by 560 days.

(21) Appl. No.: 17/534,418

(22) Filed: Nov. 23, 2021

(65) Prior Publication Data

US 2022/0202442 A1 Jun. 30, 2022

Related U.S. Application Data

(60) Provisional application No. 63/131,765, filed on Dec. 29, 2020.

(30) Foreign Application Priority Data

Sep. 30, 2021 (TW) ................ 110136416

(51) Int. Cl.
  *A61B 17/34* (2006.01)
  *A61B 34/10* (2016.01)
  *G06N 20/00* (2019.01)
(52) U.S. Cl.
  CPC .......... *A61B 17/3403* (2013.01); *A61B 34/10* (2016.02); *G06N 20/00* (2019.01); *A61B 2034/104* (2016.02); *A61B 2034/105* (2016.02)

(58) Field of Classification Search
  CPC ...... A61B 17/3403; A61B 2017/00699; A61B 2034/104; A61B 2034/105;
  (Continued)

(56) References Cited

U.S. PATENT DOCUMENTS 7,945,305 B2  5/2011  Aggarwal et al.
9,189,851 B2  11/2015  Liao et al.
(Continued)

FOREIGN PATENT DOCUMENTS

CN  100459950  2/2009
CN  102727304  10/2012
(Continued)

OTHER PUBLICATIONS

"Office Action of Taiwan Counterpart Application", issued on Sep. 28, 2022, p. 1-p. 10.
(Continued)

*Primary Examiner* — Mark D Remaly
(74) *Attorney, Agent, or Firm* — JCIPRNET

(57) ABSTRACT

A computer-assisted needle insertion system and a computer-assisted needle insertion method are provided. The computer-assisted needle insertion method includes: obtaining a first machine learning (ML) model and a second ML model; obtaining a computed tomography (CT) image and a needle insertion path, generating a suggested needle insertion path according to the first ML model, the CT image, and the needle insertion path, and instructing a needle to approach a needle insertion point on a skin of a target, wherein the needle insertion point is located on the suggested needle insertion path; obtaining a breath signal of the target, and estimating whether a future breath state of the target is normal according to the second ML model and the breath signal; and outputting a suggested needle insertion
(Continued)

period according to the breath signal in response to determining that the future breath state is normal.

16 Claims, 6 Drawing Sheets

(58) Field of Classification Search
CPC . A61B 2090/3762; A61B 34/10; A61B 90/39; G06N 20/00; G06N 3/044; G06N 3/045; G06N 3/08
See application file for complete search history.

(56) References Cited

U.S. PATENT DOCUMENTS

| | | |
|---|---|---|
| 10,398,382 B2 | 9/2019 | Sanders, III et al. |
| 2012/0226145 A1 | 9/2012 | Chang et al. |
| 2017/0224419 A1* | 8/2017 | Carrat ................ A61B 17/3403 |
| 2019/0117317 A1 | 4/2019 | Abayazid et al. |
| 2019/0175293 A1 | 6/2019 | Popovic et al. |
| 2019/0223958 A1 | 7/2019 | Kohli et al. |
| 2020/0297377 A1 | 9/2020 | Nields |

FOREIGN PATENT DOCUMENTS

| | | |
|---|---|---|
| CN | 108245244 | 7/2018 |
| CN | 108805877 | 11/2018 |
| CN | 109480967 | 3/2019 |
| CN | 109605365 | 4/2019 |
| CN | 110025379 | 7/2019 |
| CN | 110340888 | 10/2019 |
| CN | 110364238 | 10/2019 |
| CN | 111513850 | 8/2020 |
| CN | 111565632 | 8/2020 |
| JP | 2002189502 | 7/2002 |
| KR | 20110131053 | 12/2011 |
| KR | 20140110620 | 9/2014 |
| TW | 201941218 | 10/2019 |
| TW | I679996 | 12/2019 |

OTHER PUBLICATIONS

J. M. Kim et al., "Two Algorithms for Detecting Respiratory Rate from ECG Signal," World Congress on Medical Physics and Biomedical Engineering 2006, vol. 6, Jan. 2007, pp. 4069-4071.

* cited by examiner

COMPUTER-ASSISTED NEEDLE INSERTION SYSTEM AND COMPUTER-ASSISTED NEEDLE INSERTION METHOD

CROSS-REFERENCE TO RELATED APPLICATION

This application claims the priority benefit of U.S. Provisional Application No. 63/131,765, filed on Dec. 29, 2020 and Taiwan Application No. 110136416, filed on Sep. 30, 2021. The entirety of each of the above-mentioned patent applications is hereby incorporated by reference herein and made a part of this specification.

BACKGROUND

Technical Field

The disclosure relates to a computer-assisted needle insertion system and a computer-assisted needle insertion method.

Description of Related Art

With the advancement of technology, computed tomography (CT) images have been commonly used to perform surgeries such as precise visceral needle insertion or tumor ablation. However, surgeries based on CT images have some disadvantages. For example, when performing the visceral needle insertion surgery, a surgeon can usually only estimate the position, angle, or depth of the first needle insertion based on experience, such that the needle insertion path is not accurate enough. Therefore, a patient may need to have multiple CT images taken as a reference for the surgeon to calibrate the needle insertion path. In this way, the radiation dose received by the patient may exceed the standard. In addition, the breathing action of the patient may affect the surgeon in adjusting the needle insertion path, and the surgeon can only perform the surgery according to non-quantifiable indicators such as experience. The risk of surgery may increase due to the above factors.

SUMMARY

The disclosure provides a computer-assisted needle insertion system and a computer-assisted needle insertion method, which can provide a suggested needle insertion period and a suggested needle insertion path to a surgeon inserting a needle.

A computer-assisted needle insertion system of the disclosure is suitable for controlling a needle. The computer-assisted needle insertion system includes a storage medium and a processor. The storage medium stores a first machine learning model and a second machine learning model. The processor is coupled to the storage medium. The processor is configured to execute the following. A computed tomography image and a needle insertion path are obtained, a suggested needle insertion path is generated according to the first machine learning model, the computed tomography image, and the needle insertion path, and the needle is instructed to approach a needle insertion point on a skin of a target. The needle insertion point is located on the suggested needle insertion path. A breath signal of the target is obtained, and whether a future breath state of the target is normal is estimated according to the second machine learning model and the breath signal. A suggested needle insertion period is output according to the breath signal in response to determining that the future breath state is normal.

In an embodiment of the disclosure, the first machine learning model is a deep Q-learning model.

In an embodiment of the disclosure, the computed tomography image includes the needle, a marker on the skin of the target, and a target object.

In an embodiment of the disclosure, a state among a set of states of the Q-learning model includes a first coordinate of a needle tip of the needle, a second coordinate of the marker, and a third coordinate of the target object.

In an embodiment of the disclosure, a reward of the Q-learning model is associated with at least one of a first distance between the first coordinate and the third coordinate; an included angle between a unit vector formed by the first coordinate, the second coordinate, and the third coordinate and the needle insertion path; a second distance between the unit vector and the needle insertion path; a time when the first coordinate stops updating; and a third distance between the first coordinate and the skin.

In an embodiment of the disclosure, the computer-assisted needle insertion system further includes a transceiver. The transceiver is coupled to the processor. The processor is communicatively connected to a mechanical arm through the transceiver. The processor transmits an instruction to the mechanical arm through the transceiver to control the needle. An action among a set of actions of the Q-learning model includes a joint action of the mechanical arm.

In an embodiment of the disclosure, the processor selects the action corresponding to a maximum expected value of a cumulated reward of the Q-learning model from the set of actions, and updates a state of the Q-learning model according to the action to train the Q-learning model.

In an embodiment of the disclosure, the processor decides the suggested needle insertion path according to the updated state.

In an embodiment of the disclosure, the mechanical arm includes a fixture for fixing the needle. The processor instructs the mechanical arm to release the fixture through the transceiver during a period other than the suggested needle insertion period.

In an embodiment of the disclosure, the processor is further configured to execute the following. A reference breath cycle is decided according to historical data, and a sampling period is decided according to the reference breath cycle. An electrocardiography signal is sampled according to the sampling period. The electrocardiography signal is converted into the breath signal.

In an embodiment of the disclosure, the storage medium further stores a third machine learning model. The processor is further configured to execute the following. A breath parameter is extracted from the breath signal. Displacement of the second coordinate is obtained, and a time domain parameter is decided according to the displacement. Short-time Fourier transform is executed on the breath signal to generate a frequency domain parameter. Whether a long-term breath state of the target is normal is determined according to the breath parameter, the time domain parameter, and the frequency domain parameter based on the third machine learning model. Whether the future breath state of the target is normal is estimated in response to the long-term breath state being normal.

In an embodiment of the disclosure, the marker includes a first sub-marker corresponding to a first sub-coordinate and a second sub-marker corresponding to a second sub-coordinate. The time domain parameter includes at least one of first displacement of the first sub-coordinate on an X-axis; a second displacement of the first sub-coordinate on a Y-axis; a third displacement of the first sub-coordinate on a Z-axis; a first sum of the first displacement, the second displacement, and the third displacement; fourth displacement of the second sub-coordinate on the X-axis; a fifth displacement of the second sub-coordinate on the Y-axis; a sixth displacement of the second sub-coordinate on the Z-axis; a second sum of the fourth displacement, the fifth displacement and the sixth displacement; and a sum of the first sum and the second sum.

In an embodiment of the disclosure, the processor is further configured to execute the following. Whether the future breath state of the target is normal is estimated according to the time domain parameter and the frequency domain parameter based on the second machine learning model.

In an embodiment of the disclosure, the processor is further configured to execute the following. Displacement of the second coordinate is determined according to the breath signal, and a time domain parameter is decided according to the displacement. A feature signal is generated according to the time domain parameter. A period is set as a breath stagnation period in response to the feature signal being less than a threshold value during the period. The suggested needle insertion period is decided according to the breath stagnation period.

In an embodiment of the disclosure, the storage medium further stores a third machine learning model. The processor is further configured to execute the following. A second breath signal corresponding to the breath stagnation period is obtained. A second breath parameter is extracted from the second breath signal. Second displacement of the second coordinate is determined according to the second breath signal, and a second time domain parameter is decided according to the second displacement. Short-time Fourier transform is executed on the second breath signal to generate a frequency domain parameter. Whether a current breath state of the target is normal is determined according to the second breath parameter, the second time domain parameter, and the frequency domain parameter based on the third machine learning model. The breath stagnation period is set as the suggested needle insertion period in response to the current breath state being normal.

In an embodiment of the disclosure, the processor decides a needle movement time and a needle movement distance according to the suggested needle insertion period, and outputs the needle movement time and the needle movement distance.

A computer-assisted needle insertion method of the disclosure is suitable for controlling a needle. The computer-assisted needle insertion method includes the following steps. A first machine learning model and a second machine learning model are obtained. A computed tomography image and a needle insertion path are obtained, a suggested needle insertion path is generated according to the first machine learning model, the computed tomography image, and the needle insertion path, and the needle is instructed to approach a needle insertion point on a skin of a target. The needle insertion point is located on the suggested needle insertion path. A breath signal of the target is obtained, and whether a future breath state of the target is normal is estimated according to the second machine learning model and the breath signal. A suggested needle insertion period is output according to the breath signal in response to determining that the future breath state is normal.

Based on the above, the disclosure can enable the needle to approach the ideal needle insertion point on the skin of the target. The disclosure can determine whether the breath state of the target is normal according to the machine learning technology. The disclosure can also determine the breath stagnation period of the target according to the breath signal of the target, and suggest the surgeon to perform the needle insertion surgery during the breath stagnation period.

DETAILED DESCRIPTION OF DISCLOSED EMBODIMENTS

Figure 1:
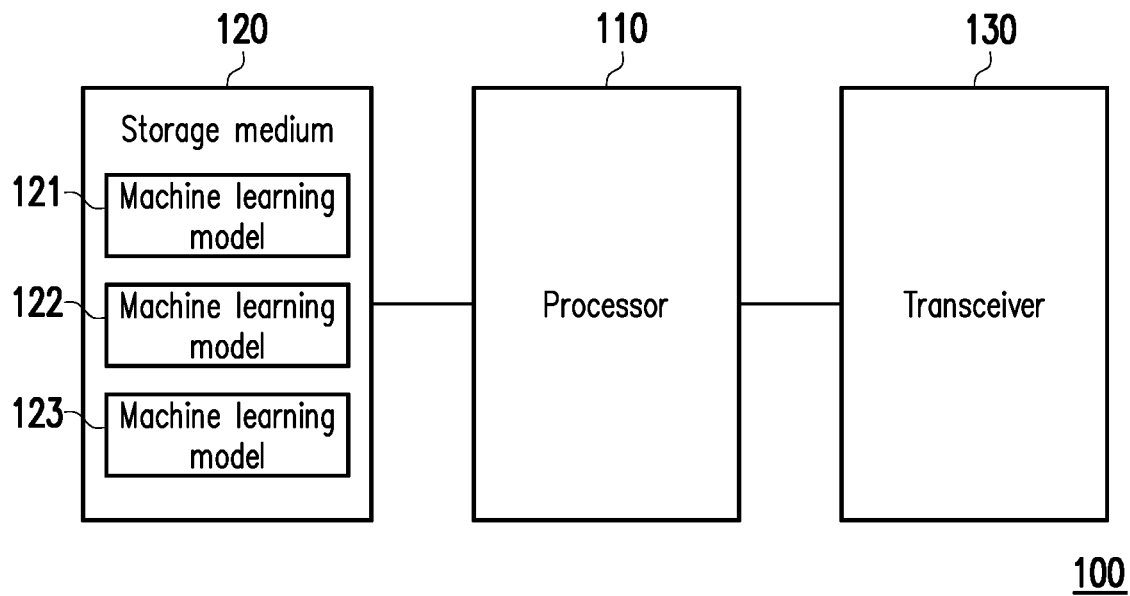
FIG. 1 is a schematic diagram of a computer-assisted needle insertion system according to an embodiment of the disclosure.

In order for the content of the disclosure to be more comprehensible, the following embodiments are specifically cited as examples on which the disclosure can be implemented. In addition, wherever possible, elements/components/steps with the same reference numerals in the drawings and embodiments represent the same or similar parts.

FIG. 1 is a schematic diagram of a computer-assisted needle insertion system 100 according to an embodiment of the disclosure. The computer-assisted needle insertion system 100 may be configured to control a needle, wherein the needle may be fixed to a mechanical arm. The computer-assisted needle insertion system 100 may control the needle by configuring the mechanical arm. The computer-assisted needle insertion system 100 may include a processor 110, a storage medium 120, and a transceiver 130.

The processor 110 is, for example, a central processing unit (CPU), other programmable general-purpose or specific-purpose micro control unit (MCU), microprocessor, digital signal processor (DSP), programmable controller, application specific integrated circuit (ASIC), graphics processing unit (GPU), image signal processor (ISP), image processing unit (IPU), arithmetic logic unit (ALU), complex programmable logic device (CPLD), field programmable gate array (FPGA), other similar elements, or a combinations of the above elements. The processor 110 may be coupled to the storage medium 120 and the transceiver 130, and access and execute multiple modules and various application programs stored in the storage medium 120.

The storage medium 120 is, for example, any type of fixed or removable random access memory (RAM), read-only memory (ROM), flash memory, hard disk drive (HDD), solid state drive (SSD), similar elements, or a combination of the above elements, and is configured to store multiple modules or various application programs that may be executed by the processor 110. In the embodiment, the storage medium 120 may store multiple modules including a machine learning model 121 (also referred to as a "first machine learning model" for suggesting a needle insertion path), a machine learning model 122 (also referred to as a "second machine learning model" for estimating whether a future breath state of a target is normal), a machine learning model 123 (also referred to as a "third machine learning model" for determining whether a current/long-term breath state of the target is normal), etc., and the functions thereof will be explained subsequently.

The transceiver 130 transmits and receives signals in a wireless or a wired manner. The transceiver 130 may also execute operations such as low noise amplification, impedance matching, frequency mixing, up or down frequency conversion, filtering, and amplification. The processor 110 may be communicatively connected to the mechanical arm for controlling the needle through the transceiver 130.

Figure 2:
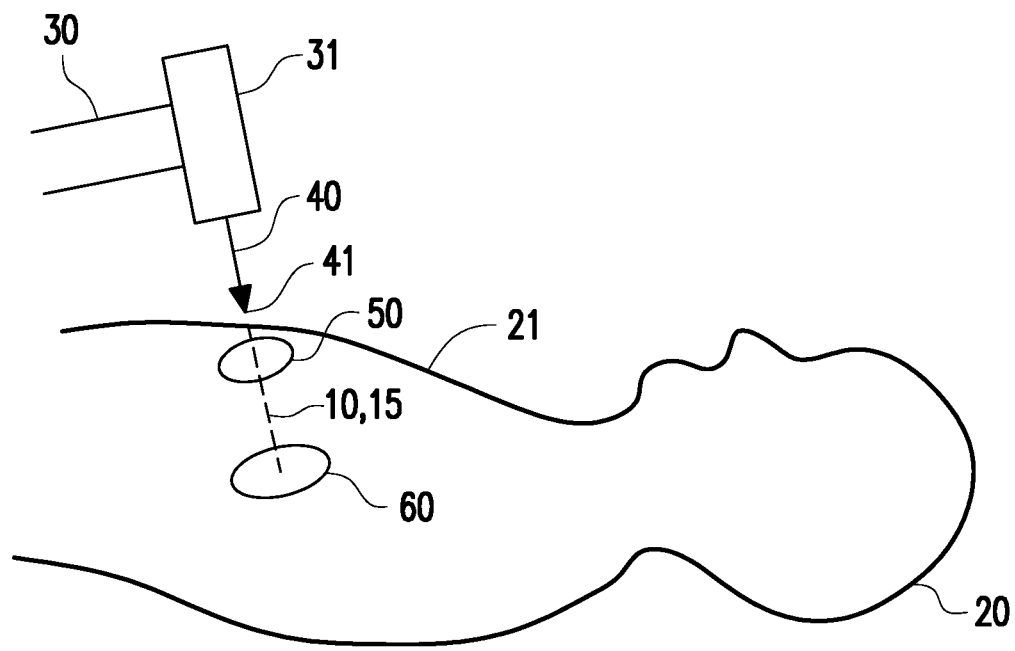
FIG. 2 is a schematic diagram of inserting a needle into a target according to an embodiment of the disclosure.

FIG. 2 is a schematic diagram of inserting a needle into a target (that is, a patient) 20 according to an embodiment of the disclosure. A mechanical arm 30 may include a fixture 31 for fixing a needle 40. The computer-assisted needle insertion system 100 may assist a surgeon to control the mechanical arm 30 to insert a needle tip 41 of the needle 40 into a target object 60. The target object 60 is, for example, a target organ in the body of the target 20.

Figure 3:
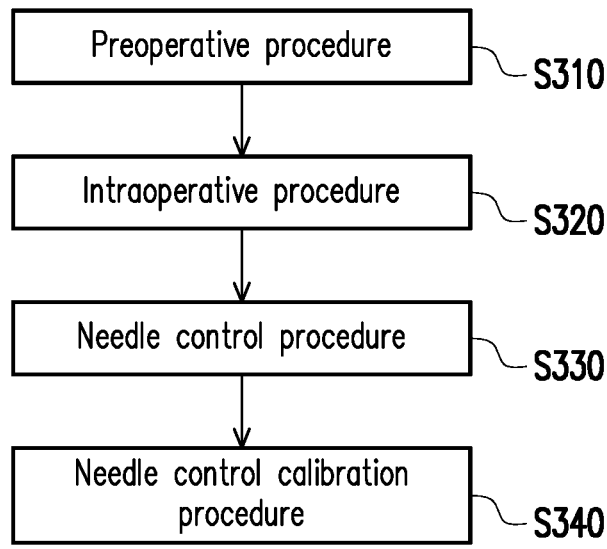
FIG. 3 is a flowchart of a computer-assisted needle insertion method according to an embodiment of the disclosure.

FIG. 3 is a flowchart of a computer-assisted needle insertion method according to an embodiment of the disclosure, wherein the computer-assisted needle insertion method may be implemented by the computer-assisted needle insertion system 100 shown in FIG. 1. In Step S310, the processor 110 may execute a preoperative procedure. In Step S320, the processor 110 may execute an intraoperative procedure. In Step S330, the processor 110 may execute a needle control procedure. In Step S340, the processor 110 may execute a needle control calibration procedure.

The processor 110 may execute the preoperative procedure (that is, Step S310) to generate a CT image. Specifically, the processor 110 may be communicatively connected to a CT imaging camera through the transceiver 130 and control the CT imaging camera to scan the target 20 to generate the CT image. The CT image may include the target 20, a label 50, and the target object 60. The processor 110 may receive the CT image from the CT imaging camera.

Figure 4:
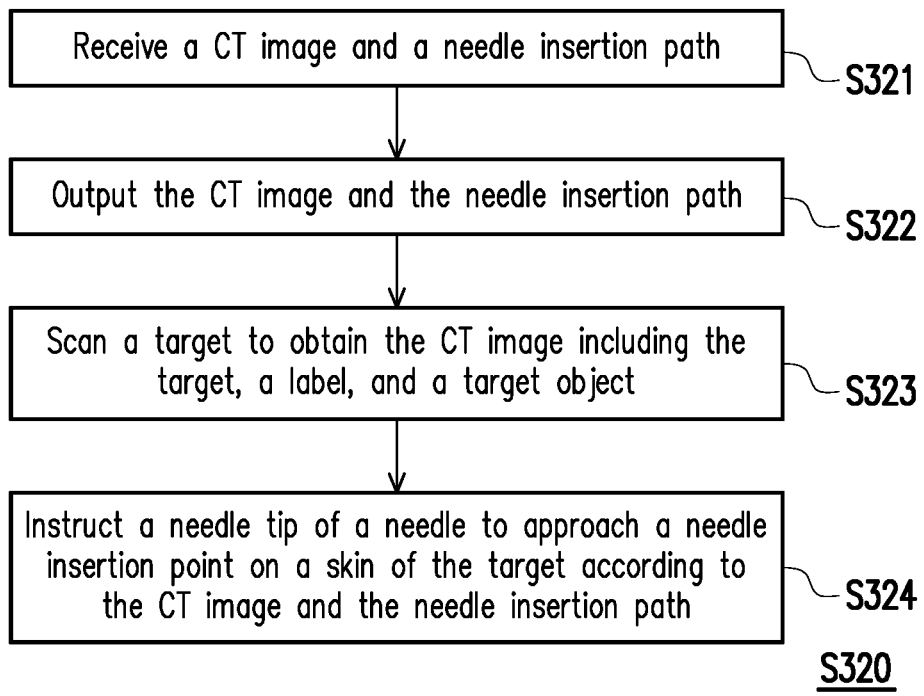
FIG. 4 is a flowchart of Step S320 according to an embodiment of the disclosure.

The processor 110 may execute the intraoperative procedure (that is, Step S320) to instruct the needle 40 to approach a needle insertion point on a skin 21 of the target 20. The ideal needle insertion point may be located at an intersection of a suggested needle insertion path 15 and the skin 21. The processor 110 may output the suggested needle insertion path 15 through the transceiver 130 for reference by the surgeon. FIG. 4 is a flowchart of Step S320 according to an embodiment of the disclosure. Step S320 may include Steps S321 to S324.

In Step S321, the processor 110 may receive the CT image and the needle insertion path 10 through the transceiver 130. For example, the processor 110 may receive the CT image from the CT imaging camera through the transceiver 130. For example, the surgeon may operate a terminal device to select the needle insertion path 10. The processor 110 may receive the needle insertion path 10 from the terminal device through the transceiver 130.

In Step S322, the processor 110 may output the CT image and the needle insertion path 10 through the transceiver 130. Specifically, the processor 110 may be communicatively connected to a display through the transceiver 130 to display the CT image for reference by the surgeon. The surgeon may confirm whether to adopt the needle insertion path 10 according to the CT image, and may paste a marker 50 on the skin 21 of the target 20 according to the needle insertion path 10, as shown in FIG. 2. For example, the surgeon may paste the marker 50 at an intersection of the needle insertion path 10 and the skin 21.

In Step S323, after the marker 50 is pasted to the target 20, the processor 110 may control the CT imaging camera to scan the target 20 to obtain the CT image including the target 20, the label 50, and the target object 60. The processor 110 may receive the CT image from the CT imaging camera through the transceiver 130. In an embodiment, the processor 110 may output the CT image and the needle insertion path 10 to the display through the transceiver 130. The display may display the CT image and the needle insertion path 10 for reference by the surgeon.

In Step S324, the processor 110 may instruct the needle tip 41 of the needle 40 to approach the needle insertion point on the skin 21 of the target 20 according to the CT image and the needle insertion path 10, wherein the needle insertion point may be located within the marker 50. In an embodiment, the processor 110 may output prompt information (for example, a prompt image or a prompt audio) through the transceiver 130, wherein the prompt information may prompt the surgeon to operate the mechanical arm 30, so that the needle tip 41 of the needle 40 approaches the needle insertion point. In an embodiment, the processor 110 may transmit an instruction to the mechanical arm 30 through the transceiver 130 to control the needle 40, so that the needle tip 41 of the needle 40 approaches the needle insertion point.

Specifically, the processor 110 may generate the suggested needle insertion path 15 according to the machine learning model 121, the CT image, and the needle insertion path 10, and instruct the needle tip 41 of the needle 40 to approach the needle insertion point, wherein the CT image may include the target 20, the label 50, and the target object 60. The needle insertion point may be located on the suggested needle insertion path 15. The machine learning model 121 may be a reinforcement learning model. In the embodiment, the machine learning model 121 is a deep Q-learning (DQN) model.

According to a Q-learning algorithm, an intelligent agent of the machine learning model 121 may transfer from a state among a set of states S to another state among the set of states S through executing a set of actions A. When executing an action in a specific state, the intelligent agent may obtain a reward. The intelligent agent of the machine learning model 121 may be implemented by the processor 110.

The state among the set of states S of the machine learning model 121 may include a coordinate of the needle tip 41, a coordinate of the marker 50, a coordinate of the target object 60, or a time stamp. The states among the set of states S may correspond to the Cartesian coordinate system or quaternion. The action among the set of actions A of the machine learning model 121 may include a joint action of the mechanical arm 30. If the mechanical arm 30 includes one or more joints, the joint action may control one or more joints of the mechanical arm 30, so as to change the coordinate of the needle tip 41. It is worth noting that in order to prevent a specific action from causing damage to the mechanical arm 30, the set of actions A may not include the joint action corresponding to the singularity of the mechanical arm 30.

The algorithm used by the machine learning model 121 is shown in Equation (1) and Equation (2), where $s_t$ is a state corresponding to a timepoint t, $a_t$ is an action corresponding to the timepoint t, $r_t$ is a reward corresponding to the timepoint t, and Q is an expected cumulated reward function. Equation (1) is used during a training period, and Equation (2) is used during a test period. The reward $r_t$ is only used during the training period, and the trained expected cumulated reward function Q is used during the test period. In an embodiment, the expected cumulated reward function Q may be a deep neural network. The processor 110 may form a training set TD (TD={$(s_t, a_t, r_t, s_{t+1})$, 1≤t≤N}) after collecting enough samples of the state $s_t$, the action $a_t$, the reward $r_t$, and a state $s_{t+1}$, and may train the expected cumulated reward function Q of the training machine learning model 121 according to N samples in the training set TD (where N is a positive integer), as shown in Equation (1).

$$Q(s_t, a_t) = r_t + \max_{a \in A} Q(s_{t+1}, a) \quad (1)$$

$$a_t = \max_{a \in A} Q(s_t, a) \quad (2)$$

The processor 110 may decide the suggested needle insertion path 15 according to the state, wherein the suggested needle insertion path 15 may be similar to the needle insertion path 10 (the surgeon selects the needle insertion path 10, and the suggested needle insertion path 15 will approach the needle insertion path 10 through the expected cumulated reward function Q), as shown in FIG. 2. Specifically, the processor 110 may optimize the coordinate of the needle tip 41, the coordinate of the marker 50, or the coordinate of the target object 60 according to Equation (2), so that the needle tip 41 approaches the needle insertion point on the skin 21 of the target 20. For example, the state $s_t$ may be a function of the coordinate of the needle tip 41, the coordinate of the marker 50, or the coordinate of the target object 60 at the timepoint t. On the other hand, the coordinate of the needle tip 41, the coordinate of the marker 50, or the coordinate of the target object 60 may be a function of the state $s_t$. The processor 110 may decide an action $a_t$ according to the state $s_t$, thereby maximizing the trained expected cumulated reward Q. The processor 110 may update the state $s_t$ according to the action $a_t$ to generate the state $s_{t+1}$. After repeatedly executing the above steps, the final state $s_t$ will be optimized. In other words, the coordinate of the needle tip 41, the coordinate of the marker 50, or the coordinate of the target object 60 will be optimized. After optimizing the coordinate of the needle tip 41, the coordinate of the marker 50, or the coordinate of the target object 60, the processor 110 may decide the suggested needle insertion path 15 according to the optimized coordinate of the needle tip 41, the optimized coordinate of the marker 50, or the optimized coordinate of the target object 60. For example, the optimized coordinate of the needle tip 41, the optimized coordinate of the marker 50, or the optimized coordinate of the target object 60 may form the suggested needle insertion path 15.

In an embodiment, the processor 110 may output reference information related to the state or the action of the machine learning model 121 to the surgeon through the transceiver 130. The surgeon may operate the mechanical arm 30 according to the reference information, so that the needle tip 41 approaches the needle insertion point. In an embodiment, the processor 110 may transmit an instruction corresponding to the state or the action of the machine learning model 121 to the mechanical arm 30 through the transceiver 130, so as to control the mechanical arm 30 to move the needle 40, so that the needle tip 41 approaches the needle insertion point.

In an embodiment, the reward of the machine learning model 121 may be related to a distance between the coordinate of the needle tip 41 and the coordinate of the target object 60. The shorter the distance, the higher the value of the reward $r_t$. In other words, the reward $r_t$ of the machine learning model 121 may be configured to train the expected cumulated reward function Q, wherein the expected cumulated reward function Q may minimize the distance between the needle tip 41 and the target object 60 (also referred to as a "first distance").

In an embodiment, the reward of the machine learning model 121 may be related to an included angle between a specific unit vector and the needle insertion path 10 of the marker 50, wherein the specific unit vector may be a unit vector formed by the coordinate of the needle tip 41, the coordinate of the marker 50, and the coordinate of the target object 60. The smaller the included angle, the higher the value of the reward. In other words, the reward of the machine learning model 121 may be configured to train the expected cumulated reward function Q, wherein the expected cumulated reward function Q may enable a line segment formed by the needle tip 41, the marker 50, and the target object 60 to be parallel to the needle insertion path 10. In an embodiment, the reward of the machine learning model 121 may be related to a distance between the specific unit vector and the needle insertion path 10 (also referred to as a "second distance"). The shorter the distance, the higher the value of the reward. In other words, the reward of the machine learning model 121 may enable the line segment formed by the needle tip 41, the marker 50, and the target object 60 to approach the needle insertion path 10.

In an embodiment, the reward of the machine learning model 121 may be related to a time when the coordinate of the needle tip 41 stops updating. The longer the time to stop updating (for example, the needle tip 41 stands still or does not move), the lower the value of the reward. In other words, the reward of the machine learning model 121 may be configured to train the expected cumulated reward function Q, wherein the expected cumulated reward function Q may impel the mechanical arm 30 to actively move the needle tip 41.

In an embodiment, the reward of the machine learning model 121 may be related to a distance between the coordinate of the needle tip 41 and the skin 21 (also referred to as a "third distance"). If the distance is less than a threshold value, the value of the reward will be greatly reduced. In other words, the reward of the machine learning model 121 may be configured to train the expected cumulated reward function Q, wherein the expected cumulated reward function Q may maintain the distance between the needle tip 41 and the skin 21 to prevent the needle tip 41 from contacting the skin 21. Therefore, before the surgeon operates the mechanical arm 30 to pierce the needle 40 into the skin 21, the mechanical arm 30 does not allow the needle 40 to contact the skin 21.

Figure 5:
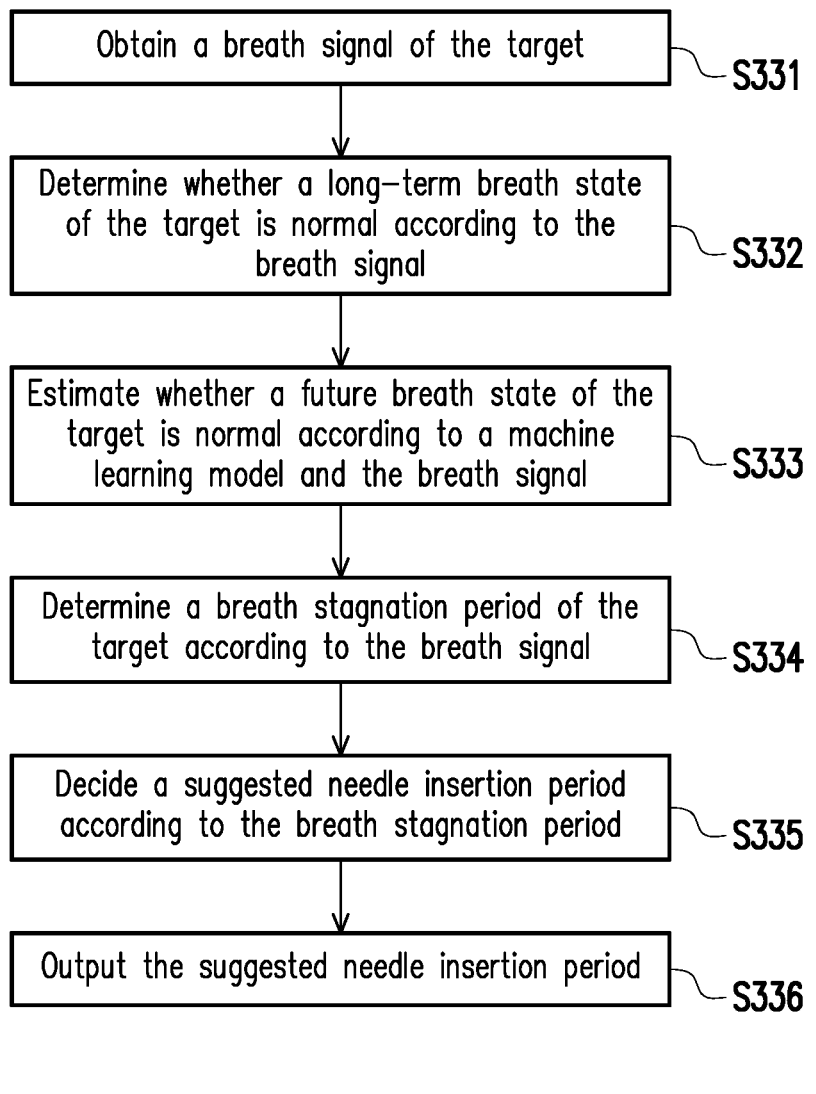
FIG. 5 is a flowchart of Step S330 according to an embodiment of the disclosure.

The processor 110 may execute the needle control procedure (that is, Step S330) to output a suggested needle insertion period according to a breath signal of the target 20 for reference by the surgeon. FIG. 5 is a flowchart of Step S330 according to an embodiment of the disclosure. Step S330 may include Steps S331 to S336.

In Step S331, the processor 110 may obtain the breath signal of the target 20 through the transceiver 130. Specifically, the processor 110 may decide a reference breath cycle according to historical data, wherein the historical data is, for example, multiple breath signals corresponding to multiple clinical subjects. The processor 110 may calculate an average breath cycle of the breath signals to generate the reference breath cycle, and may decide a sampling period according to the reference breath cycle.

After deciding the sampling period, the processor 110 may receive an electrocardiography (ECG) measurement result of the target 20 through the transceiver 130, and sample an electrocardiography signal from the measurement result according to the sampling period. The processor 110 may convert the electrocardiography signal into the breath signal of the target 20. For example, the processor 110 may convert the electrocardiogram signal into the breath signal according to the R size method or the RR method.

In Step S332, the processor 110 may determine whether the long-term breath state of the target 20 is normal according to the breath signal. If the long-term breath state of the target 20 is normal, proceed to Step S333. If a breath amplitude or cycle of the target 20 is within a normal range of a group (for example, the same age or the same gender) to which the target 20 belongs, the processor 110 may determine the long-term respiratory state of the target 20 as normal.

Figure 6:
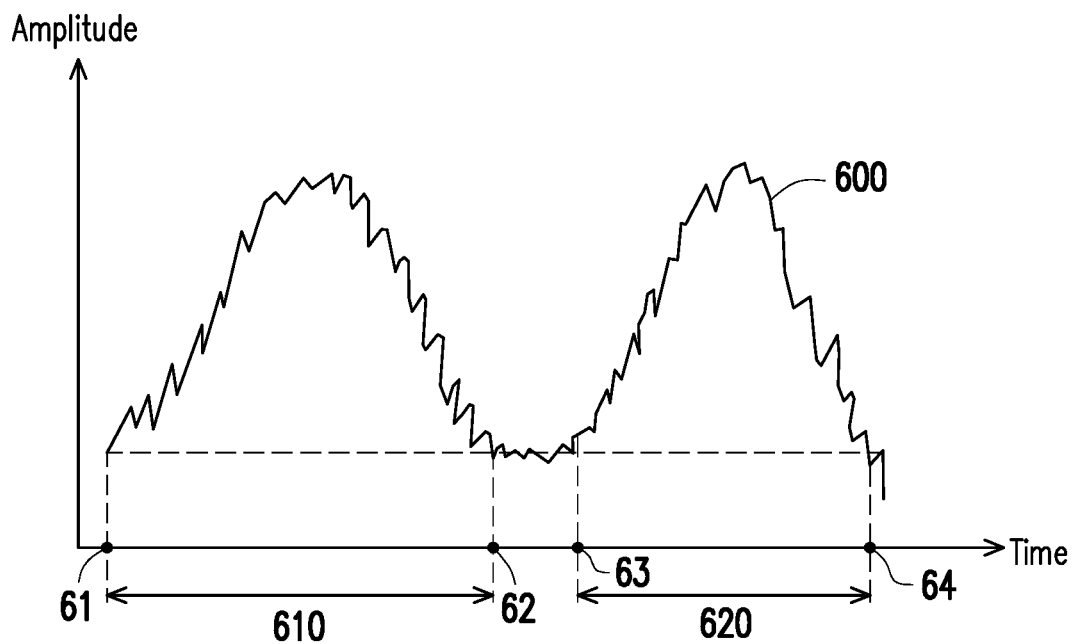
FIG. 6 is a schematic diagram of a breath signal according to an embodiment of the disclosure.

Specifically, the processor 110 may extract a breath parameter from the breath signal, wherein the breath parameter may include a breath starting timepoint, a breath stopping timepoint, the average breath cycle. FIG. 6 is a schematic diagram of a breath signal 600 according to an embodiment of the disclosure. The processor 110 may obtain N breath cycles from the breath signal 600, and calculate the average breath cycle according to the N breath cycles, where N may be any positive integer. In the embodiment, it is assumed that N is 2. The processor 110 may obtain a breath starting timepoint 61 and a breath stopping timepoint 62 from the breath signal 600. The processor 110 may calculate a breath cycle 610 according to a difference between the breath stopping timepoint 62 and the breath starting timepoint 61. In addition, the processor 110 may obtain a breath starting timepoint 63 and a breath stopping timepoint 64 from the breath signal 600. The processor 110 may calculate a breath cycle 620 according to a difference between the breath stopping timepoint 64 and the breath starting timepoint 63. The processor 110 may calculate an average value of the breath cycle 610 and the breath cycle 620 to generate the average breath cycle (unit: second).

On the other hand, the processor 110 obtains displacement of the coordinate of the marker 50 through the transceiver 130, and decides a time domain parameter according to the displacement. Specifically, the processor 110 may determine the displacement of the coordinate of the marker 50 according to the electrocardiogram signal corresponding to the breath signal 600. The processor 110 may decide the time domain parameter according to the displacement of the coordinate of the marker 50. In an embodiment, the processor 110 may first execute a low-pass filtering procedure on the breath signal to generate a filtered breath signal. The processor 110 may determine the displacement of the coordinate of the marker 50 according to the filtered breath signal.

Figure 7:
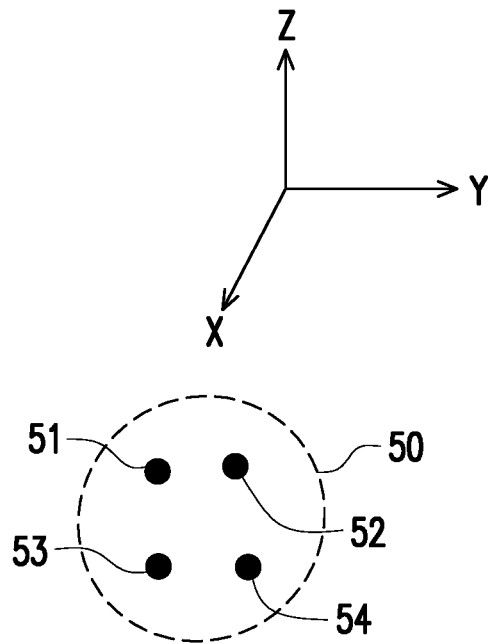
FIG. 7 is a schematic diagram of a marker according to an embodiment of the disclosure.

The time domain parameter may be associated with sub-markers of the marker 50. FIG. 7 is a schematic diagram of the marker 50 according to an embodiment of the disclosure. The marker 50 may include one or more sub-markers. In the embodiment, the marker 50 may include a sub-marker 51, a sub-marker 52, a sub-marker 53, and a sub-marker 54.

In an embodiment, the time domain parameter may be a function of time. The time domain parameter may include displacement of the sub-markers on each coordinate axis. For example, the time domain parameter may include multiple time domain features such as displacement $\Delta N_x^{51}$ of a coordinate of the sub-marker 51 (the coordinate of the sub-marker is also referred to as a "sub-coordinate") on the X-axis, displacement $\Delta N_y^{51}$ of a coordinate of the sub-marker 51 on the Y-axis, displacement $\Delta N_z^{51}$ of a coordinate of the sub-marker 51 on the Z-axis, displacement $\Delta N_x^{52}$ of a coordinate of the sub-marker 52 on the X-axis, displacement $\Delta N_{y2}^{52}$ of a coordinate of the sub-marker 52 on the Y-axis, displacement $\Delta N_z^{52}$ of a coordinate of the sub-marker 52 on the Z-axis, displacement $\Delta N_x^{53}$ of a coordinate of the sub-marker 53 on the X-axis, displacement $\Delta N_y^{53}$ of a coordinate of the sub-marker 53 on the Y-axis, displacement $\Delta N_z^{53}$ of a coordinate of the sub-marker 53 on the Z-axis, displacement $\Delta N_x^{54}$ of a coordinate of the sub-marker 54 on the X-axis, displacement $\Delta N_y^{54}$ of a coordinate of the sub-marker 54 on the Y-axis, and displacement $\Delta N_z^{54}$ of a coordinate of the sub-marker 54 on the Z-axis.

In an embodiment, the time domain parameter may include a sum of the displacements of the sub-markers on each coordinate axis. For example, the time domain parameter may include a sum $\Delta N^{51}$ ($\Delta N^{51}=\Delta N_x^{51}+\Delta N_y^{51}+\Delta N_z^{51}$) of the displacements of the coordinates of the sub-marker 51 on the X-axis, the Y-axis, and the Z-axis. The time domain parameter may include a sum $\Delta N^{52}$ ($\Delta N^{52}=\Delta N_x^{52}+\Delta N_y^{52}+\Delta N_z^{52}$) of the displacements of the coordinates of the sub-marker 52 on the X-axis, the Y-axis, and the Z-axis. The time domain parameter may include a sum $\Delta N^{53}$ ($\Delta N^{53}=\Delta N_x^{53}+\Delta N_y^{53}+\Delta N_z^{53}$) of the displacements of the coordinates of the sub-marker 53 on the X-axis, the Y-axis, and the Z-axis. The time domain parameter may include a sum $\Delta N^{54}$ ($\Delta N^{54}=\Delta N_x^{54}+\Delta N_y^{54}+\Delta N_z^{54}$) of the displacements of the coordinates of the sub-marker 54 on the X-axis, the Y-axis, and the Z-axis.

In an embodiment, the time domain parameter may include a sum of the displacements of the sub-markers on different coordinate axes. For example, the time domain parameter may include a sum $\Delta N$ ($\Delta N=\Delta N^{51}+\Delta N^{52}+\Delta N^{53}+\Delta N^{54}$) of four parameters such as the sum $\Delta N^{51}$, the sum $\Delta N^{52}$, the sum $\Delta N^{53}$, and the sum $\Delta N^{54}$.

On the other hand, the processor 110 may execute the short-time Fourier transform (STFT) on the breath signal to generate a frequency domain parameter. For example, the processor 110 may execute the short-time Fourier transform with a resolution of 128 on the breath signal 600 to generate the frequency domain parameter including 128 frequency features.

After obtaining the breath parameter, the time domain parameter, and the frequency domain parameter, the processor 110 may determine whether the long-term breath state of the target 20 is normal according to the breath parameter, the time domain parameter, and the frequency domain parameter based on the machine learning model 123. Specifically, the processor 110 may input multiple breath parameters, multiple time domain parameters, and multiple frequency domain parameters respectively corresponding to multiple timepoints into the machine learning model 123 to generate multiple output data respectively corresponding to the time-points, wherein each of the output data may represent that the current breath state is normal or the current breath state is abnormal, and multiple current breath state data are accumulated as the long-term breath state. The processor 110 may determine whether the long-term breath state of the target 20 is normal according to the multiple output data. The machine learning model 123 is, for example, a recurrent neural network (RNN) model. In an embodiment, the machine learning model 123 may be a supervised machine learning model. The processor 110 may collect multiple historical breath parameters, multiple historical time domain parameters, and multiple historical frequency domain parameters to train the machine learning model 123. The trained machine learning model 123 may determine whether the breath state of the target 20 is normal according to the breath parameter, the time domain parameter, and the frequency domain parameter.

In Step S333, the processor 110 estimates whether the future breath state of the target 20 is normal according to the machine learning model 122 and the breath signal. If the future breath state of the target 20 is normal, proceed to Step S334.

Specifically, the processor 110 may estimate the future breath state of the target 20 (for example, estimate the breath state at a time t+1, t+2, or t+3) according to the time domain parameter or the frequency domain parameter related to the breathing signal 600 (for example, the time domain parameter or the frequency domain parameter described in Step S332) based on the machine learning model 122. The processor 110 may input the time domain parameter or the frequency domain parameter into the machine learning model 122. The machine learning model 122 may output data representing that the future breath state is normal or the future breath state is abnormal according to input data. The machine learning model 122 is, for example, a recurrent neural network model. In an embodiment, the machine learning model 122 may be a supervised machine learning model. The processor 110 may collect multiple historical time domain parameters and multiple historical frequency domain parameters to train the machine learning model 122. The trained machine learning model 122 may estimate whether the future breath state of the target 20 is normal according to the time domain parameter and the frequency domain parameter.

In Step S334, the processor 110 may determine a breath stagnation period of the target 20 according to the breath signal. Specifically, the processor 110 may generate a feature signal according to the time domain parameter corresponding to the breath signal 600 (for example, the time domain parameter described in Step S332). The processor 110 may set a specific period as the breath stagnation period in response to the feature signal being less than a threshold value during the specific period. In an embodiment, the feature signal may be a feature of the displacements of the sub-markers of the marker 50 on each coordinate axis.

Figure 8:
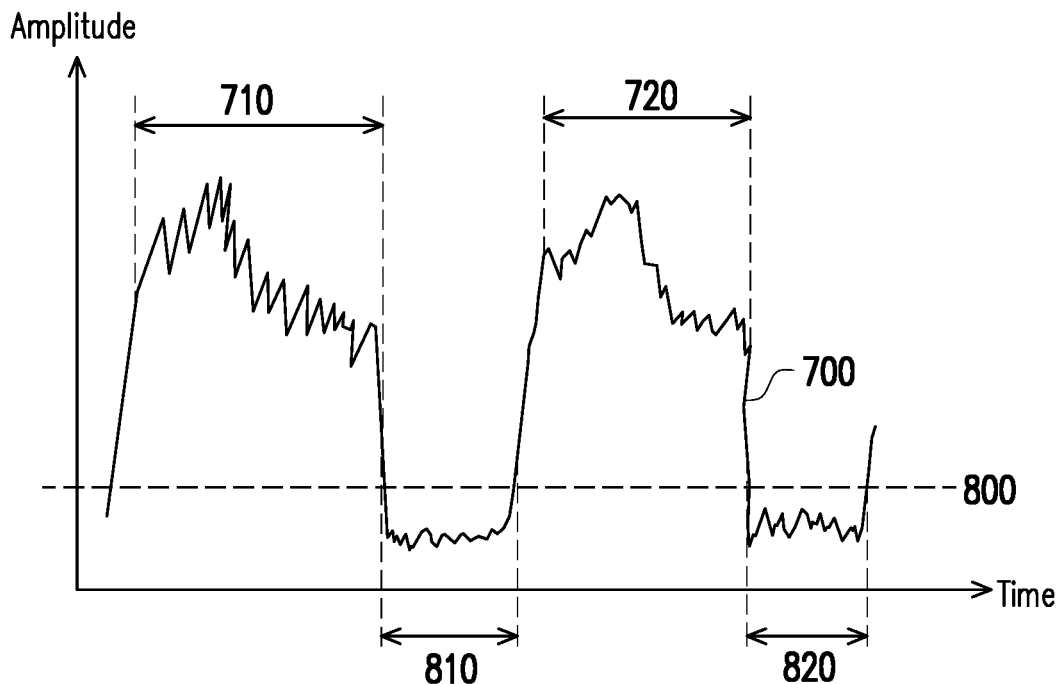
FIG. 8 is a schematic diagram of a feature signal according to an embodiment of the disclosure.

FIG. 8 is a schematic diagram of a feature signal 700 according to an embodiment of the disclosure. It is assumed that a period 710 corresponds to the breath cycle 610 and a period 720 corresponds to the breath cycle 620. The processor 110 may set the period 810 or the period 820 as the breath stagnation period of the target 20 in response to the feature signal 700 being less than a threshold value 800 during the period 810 or the period 820. Inserting the needle into the target 20 during the breath stagnation period can greatly reduce the risk of surgery.

In Step S335, the processor 110 may decide the suggested needle insertion period according to the breath stagnation period. For example, the processor 110 may select at least one of the period 810 and the period 820 as the suggested needle insertion period.

In an embodiment, the processor 110 may decide the suggested needle insertion period according to the current breath state of the target 20. Specifically, the processor 110 may obtain a breath signal (also referred to as a "second breath signal" or a "breath stagnation signal") corresponding to the breath stagnation period through the transceiver 130. For example, the processor 110 may receive an electrocardiogram signal of the target 20 corresponding to the breath stagnation period through the transceiver 130, and convert the electrocardiogram signal into the breath stagnation signal. The processor 110 may convert the electrocardiography signal into the breath stagnation signal according to the R size method or the RR method.

Then, the processor 110 may generate a time domain parameter and a frequency domain parameter according to the breath stagnation signal. For example, the processor 110 may generate the time domain parameter and the frequency domain parameter corresponding to the breath stagnation signal according to a manner similar to Step S332. The processor 110 may determine whether the current breath state of the target 20 is normal according to the time domain parameter and the frequency domain parameter based on the machine learning model 123. The processor 110 may input the time domain parameter and the frequency domain parameter into the machine learning model 123. The machine learning model 123 may output data representing that the current breath state is normal or the current breath state is abnormal according to input data. The processor 110 may set the breath stagnation period corresponding to the breath stagnation signal as the suggested needle insertion period in response to the current breath state being normal.

In Step S336, the processor 110 may output the suggested needle insertion period through the transceiver 130.

In an embodiment, in order to prevent the target 20 from being harmed, the processor 110 may instruct the mechanical arm 30 to release the fixture 31 during a period other than the suggested needle insertion period through the transceiver 130, so that the needle 40 can move along with the ups and downs of breathing of the target 20.

In an embodiment, the processor 110 may decide a needle movement time and a needle movement distance of the needle 40 according to the suggested needle insertion period. The processor 110 may output the needle movement time and the needle movement distance through the transceiver 130. For example, the processor 110 may decide that lengths of the needle movement time (or the needle movement distance) and the suggested needle insertion period are proportional.

Figure 9:
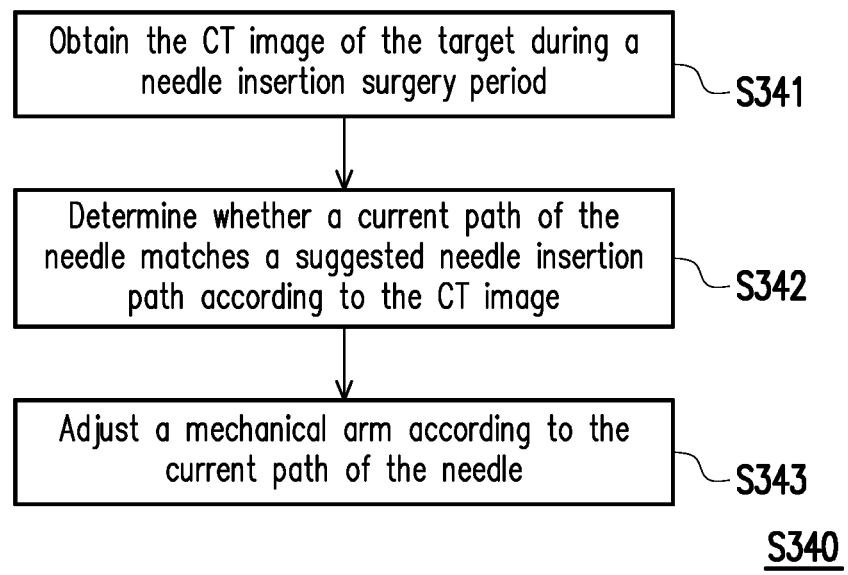
FIG. 9 is a flowchart of Step S340 according to an embodiment of the disclosure.

The processor 110 may execute the needle control calibration procedure (that is, Step S340) to ensure that the needle insertion surgery is performed smoothly. FIG. 9 is a flowchart of Step S340 according to an embodiment of the disclosure, wherein Step S340 may include Steps S341 to S343. In Step S341, the processor 110 may obtain the CT image of the target 20 during the needle insertion surgery period. The CT image may include the target 20, the needle 40, the label 50, and the target object 60. In Step S342, the processor 110 may determine whether a current path of the needle 40 matches a suggested needle insertion path 15 according to the CT image. In Step S343, the processor 110 may adjust the mechanical arm 30 according to the current path of the needle 40. Specifically, if the current path of the needle 40 matches the suggested needle insertion path 15, the processor 110 may maintain the original configuration of the mechanical arm 30. If the current path of the needle 40 does not match the suggested needle insertion path 15, the processor 110 may update the suggested needle insertion path according to the current path of the needle 40, and output the updated suggested needle insertion path through the transceiver 130.

Figure 10:
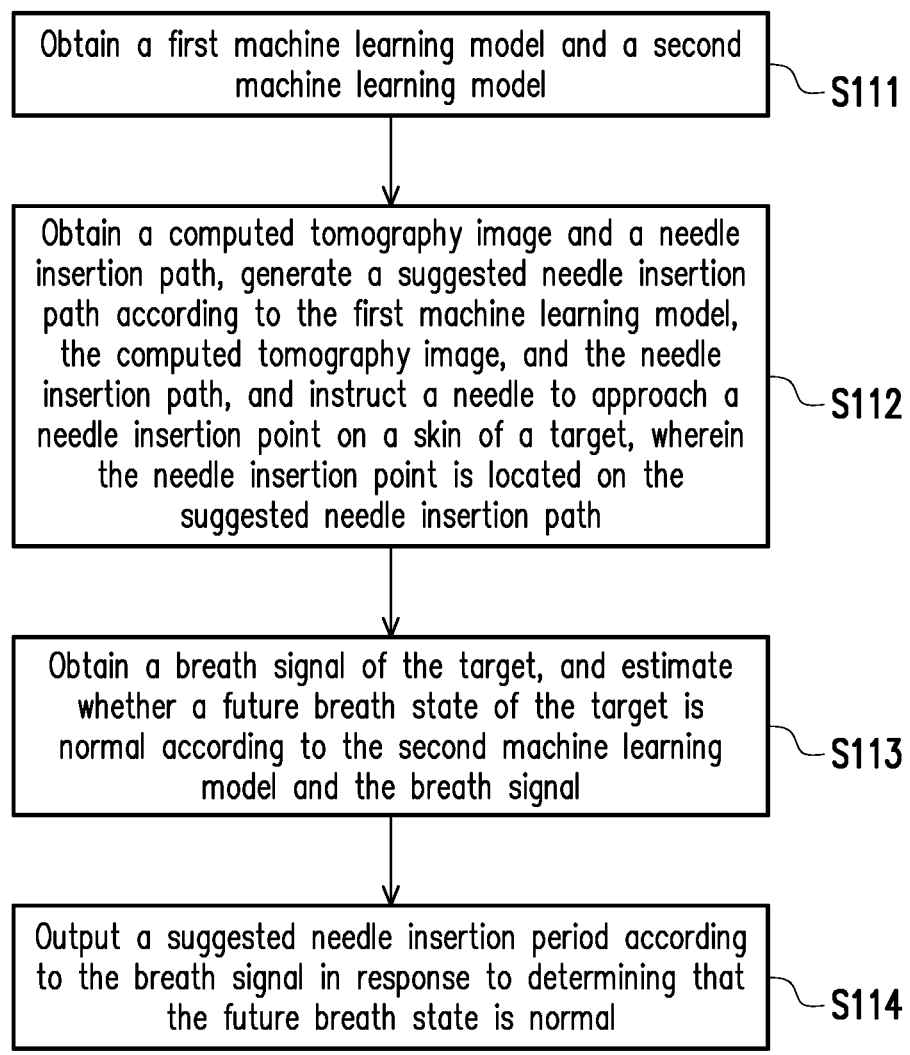
FIG. 10 is a flowchart of a computer-assisted needle insertion method according to an embodiment of the disclosure.

FIG. 10 is a flowchart of a computer-assisted needle insertion method according to an embodiment of the disclosure. The computer-assisted needle insertion method is suitable for controlling a needle, and the computer-assisted needle insertion method may be implemented by the computer-assisted needle insertion system 100 as shown in FIG. 1. In Step S111, a first machine learning model and a second machine learning model are obtained. In Step S112, a computed tomography image and a needle insertion path are obtained, a suggested needle insertion path is generated according to the first machine learning model, the computed tomography image, and the needle insertion path, and the needle is instructed to approach a needle insertion point on a skin of a target, wherein the needle insertion point is located on the suggested needle insertion path. In Step S113, a breath signal of the target is obtained, and whether a future breath state of the target is normal is estimated according to the second machine learning model and the breath signal. In Step S114, a suggested needle insertion period is output according to the breath signal in response to determining that the future breath state is normal.

In summary, the disclosure can fix the position of the needle according to the deep learning technology before performing the needle insertion surgery, so that the needle approaches the ideal needle insertion point on the skin of the target. The surgeon can accurately insert the needle into the target object according to the needle insertion point. In addition, the disclosure can determine whether the breath state of the target is normal according to the machine learning technology, so as to prevent the needle insertion surgery from being interfered in the case where the surgeon performs the needle insertion surgery when the breath state of the target is abnormal. Furthermore, the disclosure can also determine the breath stagnation period of the target according to the breath signal of the target, and suggest the surgeon to perform the needle insertion surgery during the breath stagnation period, thereby minimizing the impact of breathing of the target on the needle insertion surgery. During the period other than the breath stagnation period, the computer-assisted needle insertion system may control the mechanical arm to release the fixture for fixing the needle to reduce the damage of the needle to the body of the user.

What is claimed is:

1. A computer-assisted needle insertion system, suitable for controlling a needle, comprising:
a storage medium, storing a first machine learning model and a second machine learning model; and
a processor, coupled to the storage medium, wherein the processor is configured to:
obtain a computed tomography image and a needle insertion path, generate a suggested needle insertion path according to the first machine learning model, the computed tomography image, and the needle insertion path, and instruct the needle to approach a needle insertion point on a skin of a target, wherein the needle insertion point is located on the suggested needle insertion path;
obtain a breath signal of the target, and estimate whether a future breath state of the target is normal according to the second machine learning model and the breath signal; and
output a suggested needle insertion period according to the breath signal in response to determining that the future breath state is normal.

2. The computer-assisted needle insertion system according to claim 1, wherein the first machine learning model is a deep Q-learning model.

3. The computer-assisted needle insertion system according to claim 2, wherein the computed tomography image comprises the needle, a marker on the skin of the target, and a target object.

4. The computer-assisted needle insertion system according to claim 3, wherein a state among a set of states of the Q-learning model comprises:
a first coordinate of a needle tip of the needle, a second coordinate of the marker, and a third coordinate of the target object.

5. The computer-assisted needle insertion system according to claim 4, wherein a reward of the Q-learning model is associated with at least one of following:
a first distance between the first coordinate and the third coordinate; an included angle between a unit vector formed by the first coordinate, the second coordinate, and the third coordinate and the needle insertion path; a second distance between the unit vector and the needle insertion path; a time when the first coordinate stops updating; and a third distance between the first coordinate and the skin.

6. The computer-assisted needle insertion system according to claim 2, further comprising:
a transceiver, coupled to the processor, wherein the processor is communicatively connected to a mechanical arm through the transceiver, wherein the processor transmits an instruction to the mechanical arm through the transceiver to control the needle, wherein an action among a set of actions of the Q-learning model comprises: a joint action of the mechanical arm.

7. The computer-assisted needle insertion system according to claim 6, wherein the processor selects the action corresponding to a maximum expected value of a cumulated reward of the Q-learning model from the set of actions, and updates a state of the Q-learning model according to the action to train the Q-learning model.

8. The computer-assisted needle insertion system according to claim 7, wherein the processor decides the suggested needle insertion path according to the updated state.

9. The computer-assisted needle insertion system according to claim 6, wherein the mechanical arm comprises a fixture for fixing the needle, wherein the processor instructs the mechanical arm to release the fixture through the transceiver during a period other than the suggested needle insertion period.

10. The computer-assisted needle insertion system according to claim 1, wherein the processor is further configured to:
decide a reference breath cycle according to historical data, and decide a sampling period according to the reference breath cycle;
sample an electrocardiogramaignal according to the sampling period; and
convert the electrocardiogram signal into the breath signal.

11. The computer-assisted needle insertion system according to claim 4, wherein the storage medium further stores a third machine learning model, wherein the processor is further configured to:
  extract a breath parameter from the breath signal;
  obtain displacement of the second coordinate, and decide a time domain parameter according to the displacement;
  execute short-time Fourier transform on the breath signal to generate a frequency domain parameter;
  determine whether a long-term breath state of the target is normal according to the breath parameter, the time domain parameter, and the frequency domain parameter based on the third machine learning model; and
  estimate whether the future breath state of the target is normal in response to the long-term breath state being normal.

12. The computer-assisted needle insertion system according to claim 11, wherein the marker comprises a first sub-marker corresponding to a first sub-coordinate and a second sub-marker corresponding to a second sub-coordinate, wherein the time domain parameter comprises at least one of following:
  a first displacement of the first sub-coordinate on an X-axis; a second displacement of the first sub-coordinate on a Y-axis; a third displacement of the first sub-coordinate on a Z-axis; a first sum of the first displacement, the second displacement, and the third displacement; a fourth displacement of the second sub-coordinate on the X-axis; a fifth displacement of the second sub-coordinate on the Y-axis; a sixth displacement of the second sub-coordinate on the Z-axis; a second sum of the fourth displacement, the fifth displacement, and the sixth displacement; and a sum of the first sum and the second sum.

13. The computer-assisted needle insertion system according to claim 11, wherein the processor is further configured to:
  estimate whether the future breath state of the target is normal according to the time domain parameter and the frequency domain parameter based on the second machine learning model.

14. The computer-assisted needle insertion system according to claim 4, wherein the processor is further configured to:
  determine displacement of the second coordinate according to the breath signal, and decide a time domain parameter according to the displacement;
  generate a feature signal according to the time domain parameter;
  set a period as a breath stagnation period in response to the feature signal being less than a threshold value during the period; and
  decide the suggested needle insertion period according to the breath stagnation period.

15. The computer-assisted needle insertion system according to claim 14, wherein the storage medium further stores a third machine learning model, wherein the processor is further configured to:
  obtain a second breath signal corresponding to the breath stagnation period;
  extract a second breath parameter from the second breath signal;
  determine a second displacement of the second coordinate according to the second breath signal, and decide a second time domain parameter according to the second displacement;
  execute short-time Fourier transform on the second breath signal to generate a frequency domain parameter;
  determine whether a current breath state of the target is normal according to the second breath parameter, the second time domain parameter, and the frequency domain parameter based on the third machine learning model; and
  set the breath stagnation period as the suggested needle insertion period in response to the current breath state being normal.

16. The computer-assisted needle insertion system according to claim 1, wherein the processor decides a needle movement time and a needle movement distance according to the suggested needle insertion period, and outputs the needle movement time and the needle movement distance.

* * * * *